United States Patent [19]

Posner et al.

[11] Patent Number: 5,274,142
[45] Date of Patent: Dec. 28, 1993

[54] VITAMIN $D_3$ ANALOGUES

[75] Inventors: Gary H. Posner; Todd D. Nelson, both of Baltimore, Md.

[73] Assignee: The Johns Hopkins University, Baltimore, Md.

[21] Appl. No.: 849,716

[22] Filed: Mar. 12, 1992

[51] Int. Cl.$^5$ ............................................. C07C 401/00
[52] U.S. Cl. ..................................................... 552/653
[58] Field of Search ........................................... 552/653

[56] References Cited

U.S. PATENT DOCUMENTS 4,224,231 9/1980 DeLuca et al. .................... 552/653

Primary Examiner—Marianne M. Cintins
Assistant Examiner—Kimberly J. Kestler
Attorney, Agent, or Firm—Cushman, Darby & Cushman

[57] ABSTRACT

A vitamin $D_3$ analogue which includes at least one hydroxyalkyl substituent on the A-ring, preferably the 1-position thereof.

2 Claims, 3 Drawing Sheets

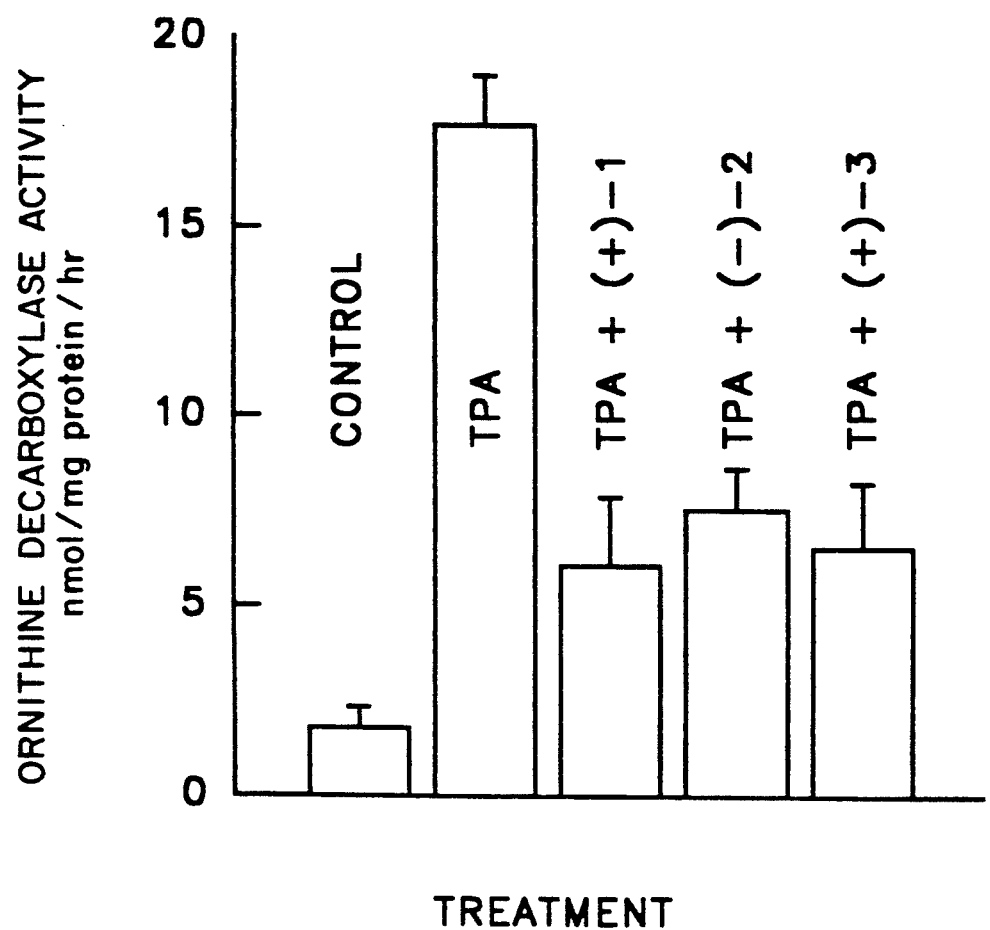

VITAMIN D₃ ANALOGUES

The present invention relates to novel biologically active vitamin $D_3$ analogues which include at least one hydroxyalkyl substituent on the A-ring.

The research disclosed herein was supported by a grant from The National Institutes of Health.

BACKGROUND OF THE INVENTION

Vitamin $D_3$ analogues have been recognized as having important biological activities. It is known, for example, that vitamin $D_3$ analogues can be used to control calcium and phosphate metabolism.

It is also known that such analogues are useful for inducing cell differentiation and for inhibiting undesired cell proliferation. For example, it is well recognized that during normal metabolism vitamin $D_3$ produces $1\alpha,25$-dihydroxyvitamin $D_3$ (calcitriol) which is a potent regulator of cell differentiation and proliferation as well as intestinal calcium and phosphorus absorption and bone calcium mobilization. Calcitriol is also known to affect the immune system and this compound, as well as a variety of synthetic vitamin $D_3$ derivatives have been used in practical, clinical chemotherapy of such diverse human illnesses as osteoporosis, cancer, immunodeficiency syndromes and skin disorders such as dermatitis and psoriasis. However, major research efforts are underway in an effort to prepare vitamin $D_3$ analogues as drugs in which calcitropic activity is effectively separated from cell growth regulation.

Numerous references can be cited as showing prior work with respect to vitamin $D_3$ analogues, calcitriol or the like. See, for example: *Vitamin D. Chemical, Biochemical, and Clinical Update,* Proceedings of the Sixth Workshop on Vitamin D, Merano, Italy, March 1985; Norman, A. W., Schaefer, K., Grigoleit, H. G., Herrath, D. V. Eds.; W. de Gruyter; New York, 1985; Brommage, R., DeLucca, H. F., *Endocrine Rev.,* 1985, 6, 491; Dickson, I., *Nature,* 1987, 325, 18; Cancela, L., Theofon, G., Norman, A. W., in *Hormones and Their Actions, Part I*; Cooke, B. A., King, R. J. B., Van der Molen, H. J. Eds.; Elaevier, Holland, 1988; Tsoukas, D. C., Provvedini, D. M., Manolagas, S. C., *Science,* (Washington, D.C.) 1984, 224, 1438; Provvedini, D. M., Tsoukas, C. D., Deftoe, L. J., Manolagas, S. C., *Science,* (Washington, D.C.) 1983, 221, 1181; *Vitamin D. Chemical Biochemical, and Clinical Endocrinology of Calcium Metabolism,* Proceedings of the Fifth Workshop on Vitamin D, Williamsburg, Va., February 1982, Norman, A. W., Schaefer, K., Herrath, D. V., Grigoleit, H. G., Eds., W. de Gruyter, New York, 1982, pp. 901–940; Calverley, M. J. in *Vitamin D: Molecular, Cellular, and Clinical Endocrinology,* Norman, A. W., Ed., de Gruyter; Berlin, 1988, p. 51; Calverley, M. J., *Tetrahedron.* 1987, 43, 4609.

Calcitriol may be structurally represented as follows:

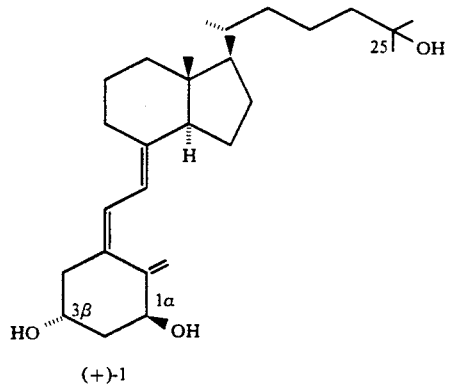

(+)-1

The upper and lower ring portions of calcitriol may be called, for ease of reference, the C/D-ring and A-ring, respectively.

Many analogues of calcitriol have been synthesized and evaluated. Among these, all the leading candidates include the $1\alpha$-hydroxyl A-ring substituent characteristic of calcitriol, i.e. they differ in the side chain attached to the D-ring of the steroid framework. Some calcitriol analogues lacking the $1\alpha$-hydroxyl group have also been prepared, e.g. the $1\beta$-hydroxyl, $1\alpha$-fluoro and the 1-unfunctionalized (i.e. 25-hydroxyvitamin $D_3$). However, these have been found to be much less biologically active than calcitriol and other synthesized $1\alpha$-hydroxy analogues. Accordingly, it appears to be axiomatic among workers in the field that the $1\alpha$-hydroxy group is essential for desirable biological activity. See, for example, *Biochem Biophys Res. Commun.,* 97:1031 (1980); *Chem. Pharm. Bull.,* 32:3525 (1984) and *Bull. Soc. Chim. France,* 11:98 (1985).

SUMMARY OF THE INVENTION

The present invention is based on the unexpected finding that the A-ring portion of vitamin $D_3$ analogues can be modified without negatively affecting the biological activity of the resulting compounds. In its broadest aspects, the invention provides vitamin $D_3$ analogues which include at least one hydroxyalkyl substituent on the ring-A. It is contemplated that this hydroxyalkyl substituent may be placed on the 1,2,3- and/or 4-positions of the A-ring. However, the preferred embodiment of the invention is the vitamin $D_3$ analogue wherein the $1\alpha$-hydroxy group is replaced by a hydroxyalkyl group of, for example, 1–6 carbon atoms.

Structurally, the preferred $D_3$ analogues of the invention may be shown as follows:

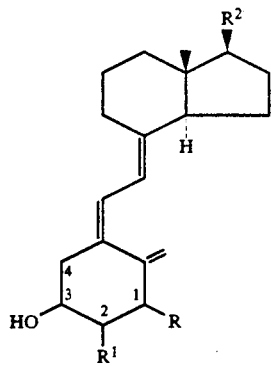

including the stereoisomers thereof, wherein R is —R³OH, R³ being straight or branched alkyl of 1 to 6 carbons; R¹ is hydrogen and R² represents the substituents completing a vitamin D₃ analogue.

However, also contemplated are the corresponding analogues which include one or more hydroxyalkyl substituents in the 2,3- and/or 4-position in lieu of, or in addition to, the hydroxyalkyl in the 1-position of the ring-A.

It will be appreciated that the D-ring may include the conventional D₃ substitution or any other known modification thereof. See, for example, the variations shown in *Cancer Research.* 50:6857–6864 (Nov. 1, 1990), the contents of which are incorporated herein by reference.

The preferred compound according to the invention is 1-hydroxymethyl-25-hydroxyvitamin D₃ represented by the formula:

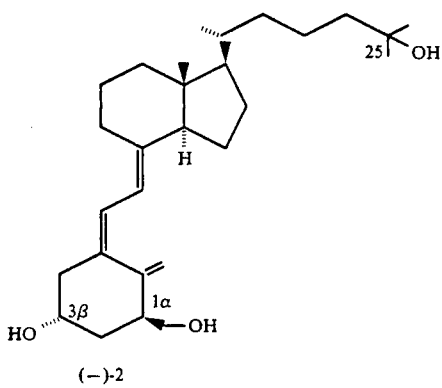

or the formula:

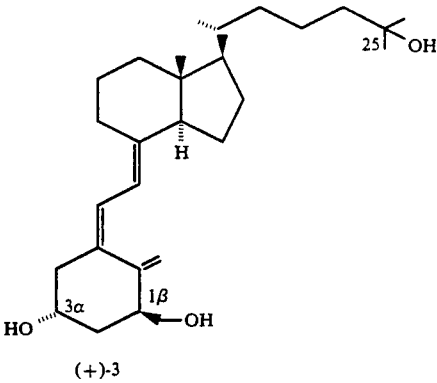

However, as noted, the invention is not to be viewed as limited to these compounds as other analogues involving the attachment of one or more additional hydroxyalkyl groups on the ring-A, with various other modifications as substituents in the ring-D, are contemplated.

DETAILED DESCRIPTION OF THE INVENTION

Figure 1:
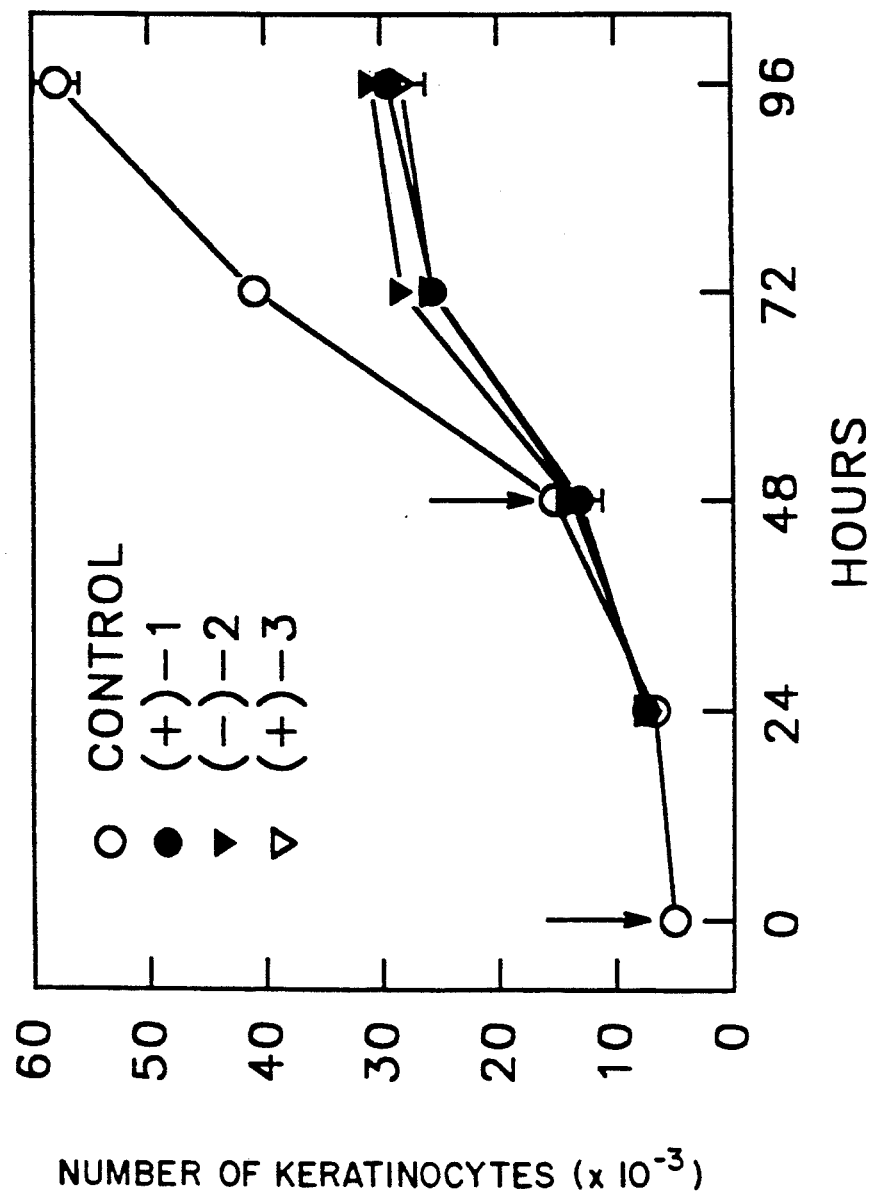
Figure 2B:
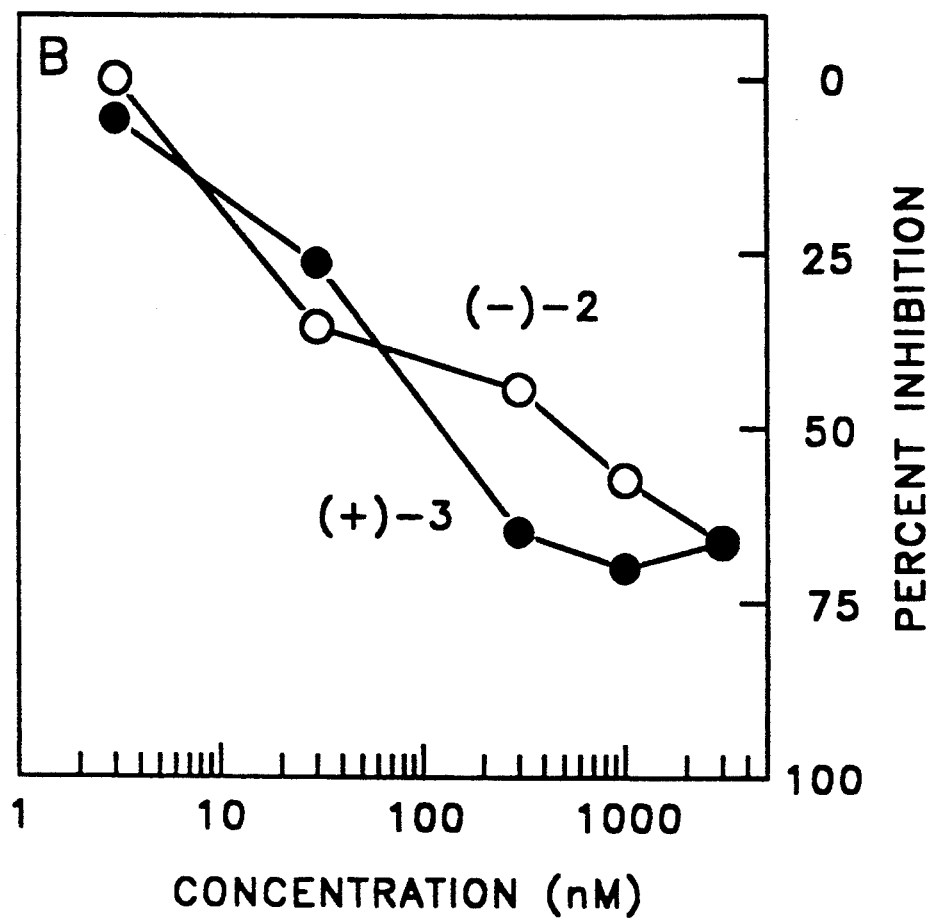

Preferred procedures for preparing the 1-hydroxyalkyl analogues of the invention are shown hereinafter although it will be appreciated that other procedures or modifications thereof can be used and will be evident to those in the art. Thus, the preparation of the two diastereomeric forms of 1-hydroxymethyl-25-hydroxyvitamin D₃, is illustrated, but not limited, by the following reaction Schemes I–III in conjunction with the examples which follow:

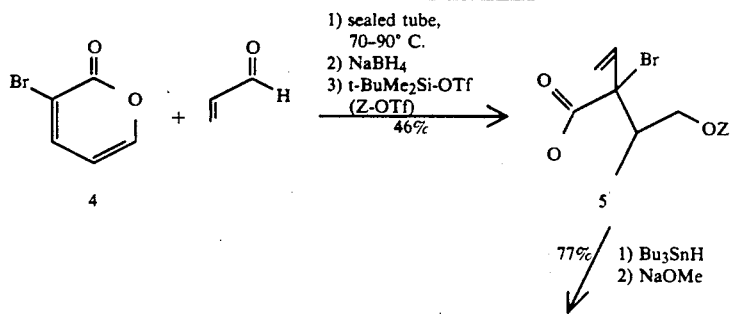

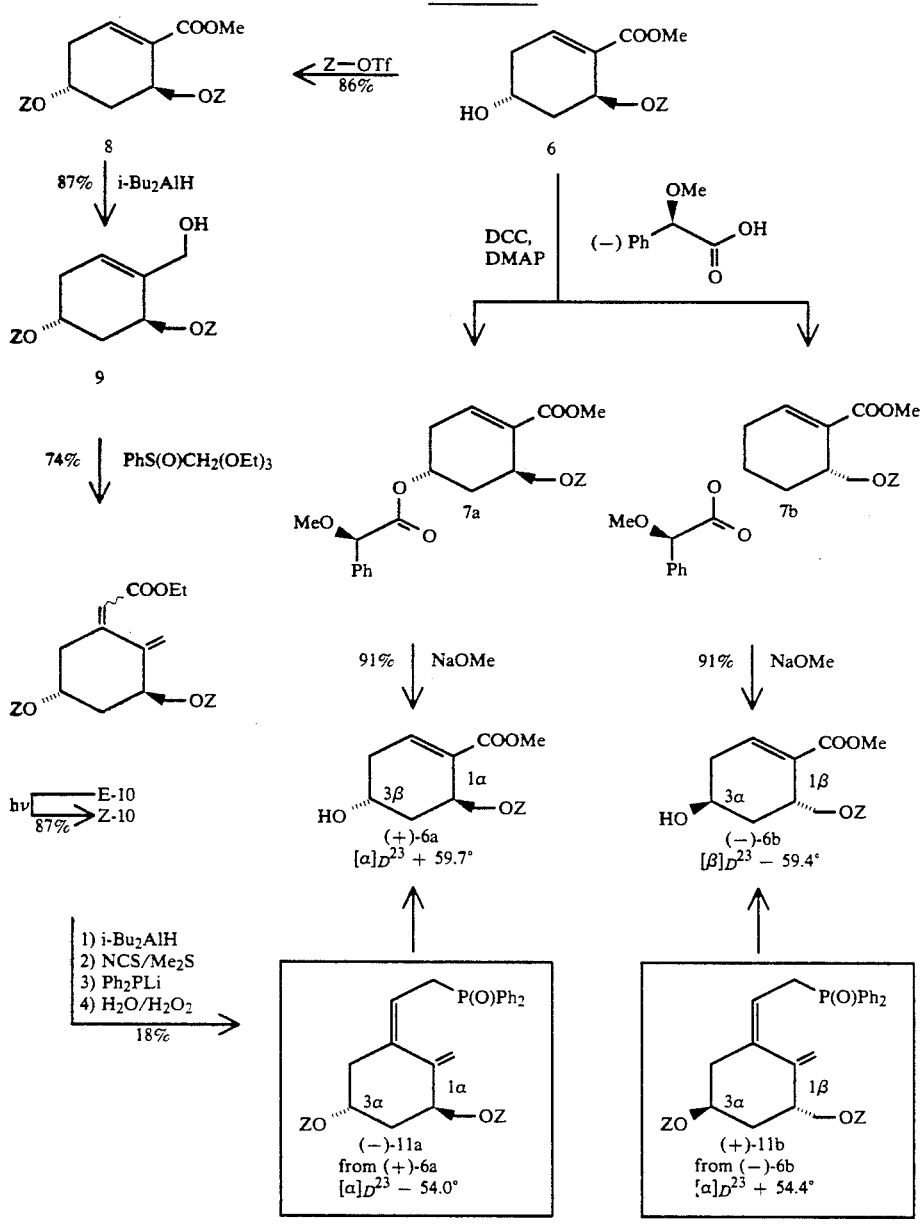

Scheme I -continued

The reaction scheme illustrated in Scheme III hereinafter utilize methodology described earlier (*J. Org. Chem.*, 56:4339 (1991); ibid 57:000 (1992); *Tetrahedron Lett.*, 32:5295 (1991); *J. Org. Chem.*, 55:3967 (1990) and *Accts. Chem. Res.*, 20:72 (1987)) to prepare ring-A phosphine oxide 11 for Horner-Wittig coupling with C,D-ring ketone 12 in a convergent approach to the vitamin $D_3$ family that was pioneered by Lythgoe et al (*J. Chem. Soc.*, Perkin I, 2608 (1977)).

The preparation process begins, as shown in Scheme I, using ambiphilic (chameleon-like) 3-bromo-2-pyrone (4) to undergo regiospecific, and stereoselective Diels-Alder cycloaddition with acrolein under sufficiently mild thermal conditions (70°-90° C.) to allow isolation on gram scale of the desired, unsaturated, bridged, bicyclic lactone adduct. Because this bicyclic aldehyde was unstable to chromatography, it was immediately reduced and then O-silylated to give chromatographically stable, crystalline, bicyclic, primary alcohol derivative 5 in 46% overall yield. Reductive cleavage of the bridgehead carbon-bromine bond was achieved in high yield under neutral radical conditions using tributyltinhydride and azobisisobutyronitrile (AIBN). The halogen-free bicyclic lactone product is the synthetic equivalent of the product derived from 2-pyrone itself cycloadding to acrolein, a Diels-Alder reaction that requires high pressures and that cannot be accomplished simply by heating because of loss of $CO_2$ from the lactone bridge. Basic methanolysis of the lactone bridge and in situ conjugation of the carbon-carbon double bond gives the conjugated cyclohexene ester alcohol 6. Resolution of this alcohol 6 is achieved via formation and separation by preparative HPLC and preparative tlc of diastereomeric esters 7a and 7b, derived from enantiomerically pure α-methoxyphenylacetic acid. Analytical HPLC indicated purified diastereomer 7a to have a diastereomeric excess (d.e.) of 98.8% and 7b of 96.5%. Methanolysis of diastereomeric esters 7a and 7b separately gave back the original alcohol 6 as a pair of enantiomers, 6a and 6b; each enantiomer was carried on separately.

The absolute stereochemistry of enantiomer 6b (and therefore also 6a) has been assigned by chemical correlation with a closely related compound of established absolute configuration (*J. Chem. Soc.*, (C), 2352 (1971)), as outlined in Scheme II.

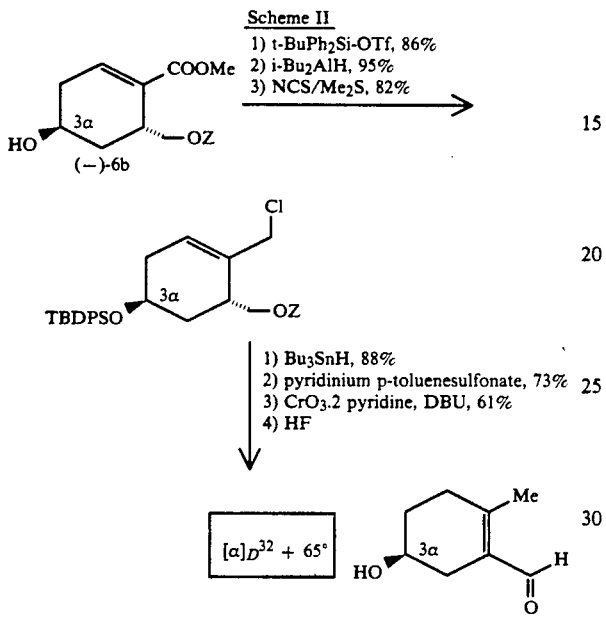

Referring back to Scheme I, O-silylation of alcohols 6 gave bis-silyl ethers 8, and then reduction of the conjugated methyl ester functionality produced allylic alcohols 9. [3,3]-Sigmatropic rearrangement using sulfinyl orthoester allowed efficient, one-flask, regiospecific formation of 2-carbon-extended conjugated dienoate esters 10 (*J. Org. Chem.*, 56:6981 (1991)). This mixture of geometric isomers was photochemically isomerized into the desired Z-10. Based on literature precedent (*J. Org. Chem.*, 51:3098 (1986)), dienoate esters 10 were reduced, chlorinated, converted into the corresponding phosphines, and finally oxidized to give ring-A phosphine oxides 11 as two enantiomers (11a and 11b) having almost equal but opposite specific rotations of approximately 54°.

Lythgoe-type coupling (*J. Chem. Soc.*, Perkin I, 2608 (1977)) of 60–100 mg of ring-A phosphine oxides 11a and 11b with enantiomerically pure ring-C,D chiron 12 was followed immediately by fluoride-promoted desilylation to form (−)-1α-hydroxymethyl-25-hydroxyvitamin D3 [(−)-2] and (+)-1β-hydroxymethyl-3α,25-hydroxy analogue (+)-3 in good yields (Scheme III). Two aspects of this coupling should be noted in particular. First, a systematic study of bases used to deprotonate phosphine oxides like 11 (e.g., MeLi, MeLi·TMEDA, n-BuLi, PhLi, LDA) showed PhLi to be best as determined by the yield of the coupled triene product. Second, the scale of the coupling reaction was critical to its success. Thus, while coupling using 60–100 mg of ring-A phosphine oxide proceeded routinely in good yields, coupling on 10–20 mg scale proceeded poorly even if such special precautions were taken such as scrupulous drying of the gaseous nitrogen or argon gas used as the atmosphere above the reaction mixture, scrupulous drying of solvents and reagents, use of molecular sieves, and azeotroping off any adventitious water by adding and removing benzene from the A and the C,D-ring units repeatedly.

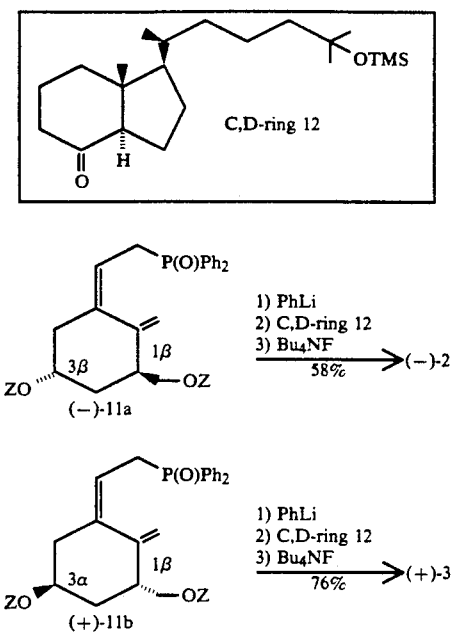

While both 1-hydroxymethyl-25-hydroxyvitamin D3 diastereomers (−)-2 and (+)-3 demonstrate useful biological activity, it is surprising to find that there are considerable physical difficulties between these diastereomers. For example, whereas 1α-hydroxymethyl diastereomer (−)-2 is easily crystallized, 1β-hydroxymethyl diastereomer (+)-3 is very difficult to crystallize. This difference in crystallinity offers a significant advantage since a mixture of diastereomers (−)-2 and (+)-3, produced from racemic ring-A phosphine oxide 11 and enantiomerically pure ring-C,D chiron 12, could be induced to yield crystals of only diastereomer (−)-2. Also, 1α-hydroxymethyl diastereomer (−)-2 demonstrates unexpectedly poor solubility in such organic solvents as methylene chloride, chloroform and methanol. Nevertheless, both hydroxymethyl diastereomers (−)-2 and (+)-3 have extremely similar UV and high field $^1$H and $^{13}$C NMR spectra as well as extremely similar chromatographic properties.

EXAMPLE 1

Bromobicyclic Lactone 5

A 25 mL hydrolysis tube was charged with 1.43 g (8.2 mmol, 1.0 eq.) of 3-bromo-2-pyrone 4, 3.69 g (65.7 mmol, 8.0 eq.) of acrolein, 23.0 mg of barium carbonate and 10 mL of methylene chloride. This was sealed under nitrogen and warmed to 70°–90° C. for 91 hours with constant stirring. Examination of an aliquot of the reaction mixture by 400 MHz $^1$H NMR indicated that complete formation of a single bicycloadduct had occurred. A stream of nitrogen was then blown over the reaction mixture so as to remove the acrolein. After holding this under high vacuum, the crude product was diluted with methylene chloride/diethyl ether (ca. 1:1) and passed through a plug of celite. The solvent was evaporated to give 3.32 g of a yellow oil which was dissolved in 50 mL ethanol and 20 mL of diglyme and cooled to −78° C. (dry ice/acetone) under argon. To this, a solution of 476 mg (21.6 mmol, 1.5 eq.) of $NaBH_4$ in 8 mL of ethanol was added. After stirring for 30 minutes, the mixture was diluted with methylene chloride and then 4 mL of saturated aqueous ammonium chloride was added. After warming to room temperature, this mixture was dried over anhydrous magnesium sulfate, filtered through a plug of celite, and purified by column chromatography (silica gel, 20% to 50% ethyl acetate/hexane) to afford 1.42 g of a yellow oil which was immediately dissolved in 20 mL of anhydrous methylene chloride under argon and cooled to 0° C. To this 0.75 mL (6.4 mmol, 1.05 eq.) of 2,6-lutidine was added followed by the addition of 1.5 mL (6.5 mmol, 1.07 eq.) of tert-butyldimethylsilyl trifluoromethanesulfonate. This was stirred for 30 minutes, warmed to room temperature, diluted with methylene chloride, washed with water, the organic portion dried over magnesium sulfate, and the solvent evaporated. Purification by silica gel column chromatography (10 to 20% ethyl acetate/hexane) afforded 1.32 g (3.8 mmol, 46%) of the silyloxy bromo bicycloadduct 5 as a white solid (Rf=0.7, 50% ethyl acetate/hexane), mp 100.5°-102° C. $^1H$ NMR ($CDCl_3$) δ 6.37-6.40 (m, 1H), 6.33 (dd, 8, 5 Hz, 1H), 5.18-5.22 (m, 1H), 3.96 (dd, J=10.1, 3.5 Hz, 1H), 3.65 (dd, J=10.1, 7.1 Hz, 1H), 2.43-2.49 (m, 1H), 2.31-2.37 (m, 1H), 1.91 (ddd, J=13.2, 3.9, 1.3 Hz, 1H), 0.86 (s, 9H), 0.05 (s, 3H), 0.04 (s, 3H); $^{13}C$ NMR ($CDCl_3$) δ 169.0, 136.4, 130.4, 73.5, 64.3, 62.1, 41.1, 31.2, 25.7 (3C), 18.1, −5.4, −5.5; FT-IR ($CHCl_3$) 1763 $cm^{-1}$; HRMS, m/z (M+-t-Bu) calcd for $C_{14}H_{23}O_3SiBr$ 288.9896, found 288.9901.

EXAMPLE 2

Hydroxy α, β-Unsaturated Ester 6 (from 5)

To a 25 mL flame-dried round-bottomed flask 179.6 mg (0.52 mmol, 1.0 eq.) of silyloxy bromo bicycloadduct 3, and a total of 0.20 mL of tri-n-butyltin hydride, 15 mg of azobisisobutyronitrile (AIBN), and 4.0 mL of anhydrous benzene was added and refluxed (placed in a preheated oil bath) for a total of 75 minutes. This was cooled to room temperature and then diluted with wet ether. A few drops of 1,8-diazabicyclo[5.4.0]undec-7-ene (DBU) were added and the mixture stirred for 5 minutes at which time the white precipitate was removed by filtration through a plug of silica gel with ether. The solvent was evaporated and the resulting oil placed in a 50 mL flame-dried round-bottomed flask under argon. The oil was dissolved in 3 mL of anhydrous tetrahydrofuran (THF) and cooled to −45° C. To this, 0.6 mL of a freshly prepared sodium methoxide solution (20 mg of sodium in 4.0 mL of anhydrous methanol) was added and stirred at −45' C. for 2.5 hours and then at 25° C. for 1 hour. The reaction mixture was diluted with methylene chloride, quenched with saturated aqueous ammonium chloride, dried over anhydrous magnesium sulfate, filtered, and the solvent evaporated. Purification by silica gel chromatography afforded 119.2 mg (0.40 mmol, 77%) of hydroxy ester 6 as a colorless oil (Rf=0.2, 25% ethyl acetate/hexane). $^1H$ NMR ($CDCl_3$ δ 6.94 (ddd, J=5, 3, 1 HZ, 1H), 4.20-4.12 (m, 1H), 3.72 (s, 3H), 3.74-3.71 (m, 1H), 3.50 (dd, J=10.0, 8.0 Hz, 1H), 2.90 (bs, 1H), 2.60 (dtdd, j=19.2, 6, 1.6, 1 Hz, 1H), 2.23 (dddd, J=12.4, 4, 2.8, 1.6 Hz, 1H), 2.09 (dddd, J=19.2, 8.8, 3.0, 2.0 Hz, 1H), 1.65 (bs, 1-OH, this signal disappears upon $D_2O$ quench), 1.57 (ddd, J=12.4, 11.2, 6 Hz, 1H), 0.87 (s, 9H), 0.03 (s, 3H), 0.01 (s, 3H); $^{13}C$ NMR ($CD_2Cl_2$) δ 167.4, 139.9, 130.5, 65.1, 63.6, 51.8, 38.1, 35.6, 33.8, 26.1 (3C), 18.5, −5.3, −5.4; FT-IR (thin film) 3412, 1716 $cm^{-1}$; HRMS, m/z (M+-t-Bu) calcd for $C_{15}H_{28}O_4Si$ 243.1053, found 243.1059.

EXAMPLE 3

Hydroxy α, β-Unsaturated Ester 6 (from 7)

A round-bottomed flask was charged with 0.632 g (1.41 mmol) of the diester 7b which was dissolved in 10 mL of tetrahydrofuran and 10 mL of methanol and then cooled to 0° C. To this, 0.20 mL of a freshly prepared sodium methoxide stock solution (32.1 mg of sodium in 5.0 mL of methanol) was added and rapidly stirred for 1 hour and then warmed to room temperature. Rapid stirring was maintained and the progress of the reaction was monitored by TLC. Periodic addition of sodium methoxide stock solution was made until the reaction was complete (ca. 8 hours). Most of the solvent was evaporated and the mixture was diluted with diethyl ether and passed through a two-inch plug of silica gel. Purification by silica gel column chromatography (25% to 75% ethyl acetate/hexane) gave 0.386 g (1.28 mmol, 91%) of the hydroxy ester (+)-6a as a colorless oil: $[α]_D^{23°\,C.}$+59.7° (c=0.082, $CH_2Cl_2$, d.e. 98.8%

The same procedure was used for the conversion of 0.900 g (2.01 mmol) of the diester 7b into 0.548 g (1.82 mmol, 91%) of the hydroxy ester (−)-6b as a colorless oil:

$[α]_D^{23°\,C.}$−59.4° (c=0.085, $CH_2Cl_2$, d.e. 98.8%

EXAMPLE 4

α-Methoxyphenylacetic Esters 7a and 7b

To flame-dried 250 mL round-bottomed flask 3.11 g (10.4 mmol of hydroxy ester 6, 2.06 g (12.4 mmol, 1.2 eq) of (R)-(−)-α-methoxyphenyl acetic acid, 2.45 g (11.9 mmol, 1.15 eq) of 1,3-dicyclohexylcarbodiimide, and 0.15 g (1.2 mmol, 0.1 eq) of 4-dimethylaminopyridine were dissolved in 150 mL of anhydrous $Et_2O$ under argon. This reaction mixture was stirred at room temperature for 12 h. The white precipitate was then removed by filtration, the organic layer was washed twice with water, dried over $MgSO_4$, and the solvent removed by rotary evaporation to leave a very light yellow oil. All impurities were removed from the diastereomeric ester 7a and 7b by silica gel column chromatography (0–20% EtOAc/hexane). The diastereomers were then separated by preparative normal phase HPLC (4.5% EtOAc/hexane, 30 mL/min) and by preparative thick layer chromatography (PTLC, multiple elutions with 15% EtOAc/hexane, 1500μ plates). On a preparative scale, the diastereomers overlapped on both HPLC and PTLC; therefore, fractions were cut and repurified by numerous injections (ca. 8) and applications, respectively. The diastereomeric excess (d.e.) of fractions was deduced by analytical normal phase HPLC (7a: $R_T$=13.4; 7b: $R_T$=15.1, 1.0 mL/min, 10% EtOAc/hexane). A 1.09 g (2.43 mmol, 23%) sample of 7a (d.e. 98.5%) and a 0.90 g (2.01 mmol, 19%) sample of 7b (d.e. 96.5%) were obtained. A 1.22 g (2.72 mmol, 26%) mixture of 7a and 7b was not adequately separated so as to be used in the subsequent synthetic transformations. 7a: $^1H$ NMR ($CDCl_3$) δ 7.44-7.32 (m, 5H), 6.80 (ddd, J=4.7, 3.35, 1.1 Hz, 1H), 5.34-5.24 (m, 1H), 4.75 (s, 1H), 3.72 (s, 3H), 3.69 (d, J=3.4 Hz, 1H), 3.57 (dd, J=10, 7.2 Hz, 1H), 3.41 (s, 3H), 2.90 (bs, 1H), 2.57–2.51 (m, 1H), 2.20–2.15 (m, 1H), 1.95 (dddd, J=19.1, 8.1, 3.35, 1.9 Hz, 1H), 1.72 (ddd, J=12.8, 11.2, 6.0 Hz, 1H), 0.85 (s, 9H), 0.02 (s, 3H), 0.01 (s, 3H); $^{13}$C NMR (CDCl$_3$) δ 169.9, 166.5, 137.9, 136.1, 130.0, 128.4, 128.3 (2C), 126.9 (2C), 82.4, 67.6, 64.3, 57.1, 51.3, 36.7, 30.9, 29.7, 25.7 (3C), 18.0, −5.7, −5.8; FT-IR (thin film) 1749, 1716 cm$^{-1}$; HRMS, m/z (M+-t-Bu) calcd for C$_{24}$H$_{36}$O$_6$Si 391.1577, found 391.1580. 7b: $^1$H NMR (CDCl$_3$) δ 7.43–7.31 (m, 5H), 6.88 (ddd, J =4.75, 3.3 1 Hz, 1H), 5.29–5.21 (m, 1H), 4.73 (s, 1H), 3.71 (s, 3H), 3.64 (dd, J=9.9, 3.5 Hz, 1H), 3.52 (dd, J=9.9, 7.1 Hz, 1H), 3.40 (s, 3H), 2.77 (bs, 1H), 2.67 (dddd, J=19, 6, ≈4.75, 1 Hz, 1H), 2.16 (ddd, J=19, 8, 3.3, 2 Hz, 1H), 2.00 (m, 1H), 1.59 (12.8, 11.0, 6, 1H), 0.81 (s, 9H), −0.03 (s, 3H), −0.07 (s, 3H); $^{13}$C NMR (CDCl$_3$) δ 170.1, 166.7, 138.1, 136.2, 130.3, 128.6, 128.5 (2C), 127.0 (2C), 82.5, 67.8, 64.3, 57.2, 51.5, 36.7, 31.4, 29.6, 25.7 (3C), 18.1, −5.6, −5.7; FT-IR (thin film) 1749, 1716 cm$^{-1}$; HRMS, m/z (M+-t-Bu) calcd for C$_{24}$H$_{36}$O$_6$Si 391.1577, found 391.1576.

EXAMPLE 5

Bis Silyloxy α,β-Unsaturated Ester 8

In a 50 mL flame-dried round bottomed flask 202.5 mg (0.67 mmol, 1.0 eq.) of hydroxy ester 6 was dissolved in 15 mL of anhydrous methylene chloride under argon. To this 0.100 mL (0.84 mmol, 1.25 eq.) of 2,6-lutidine was added and stirred for 3 minutes followed by the addition of 0.195 mL (0.84 mmol, 1.25 eq.) of tert-butyldimethylsilyl trifluoromethanesulfonate. After 30 minutes, the solvent was evaporated and purification by silica gel column chromatography (5 to 10% ethyl acetate/hexane) gave 240.4 (0.58 mmol, 86%) of the silyloxy ester 8 as a colorless oil (Rf=0.6, 10% ethyl acetate/hexane). $^1$H NMR (CDCl$_3$) δ 6.92 (ddd, J=5.2, 2.8, 1 Hz, 1H), 4.15 (m, 1H), 3.72–3.69 (m, 1H), 3.71 (s, 3H), 3.52 (dd, J=9, 8 Hz, 1H), 2.76 (bs, 1H), 2.47 (dtd, J=19.2, ca. 5.2, 1 Hz, 1H), 2.17–2.12 (m, 1H), 2.13–2.05 (dddd, J=19.2, 9, 2.8, 2.0 Hz, 1H), 1.58–1.51 (ddd, J=12.8, 11.2, 2.0, Hz, 1H), 0.88 (s, 9H), 0.87 (s, 9H), 0.07 (s, 3H), 0.06 (s, 3H), 0.02 (s, 3H), 0.01 (s, 3H); $^{13}$C NMR (CD$_2$Cl$_2$) δ 167.4, 140.3, 130.4, 65.3, 64.6, 51.7, 38.4, 36.5, 34.6, 26.1 (6C), 18.6, 18.5, −4.4 to −5.3 (4C); FT-IR (thin film) 1716 cm$^{-1}$; HRMS, m/z (M+-t-Bu) calcd for C$_{21}$H$_{42}$O$_4$Si$_2$ 357.1917, found 357.1922.

(−) -8 from (−)-6b: $[α]_D^{23°}$ $^C$ −46.7° (c=0.094, CH$_2$Cl$_2$, d.e. 96.5%)

(+) -8 from (+)-6a: $[α]_D^{23°}$ $^C$ −47.1° (c=0.100, CH$_2$Cl$_2$, d.e. 98.8%)

EXAMPLE 6

Dienoates E-10 and Z-10

A flame-dried 50 mL round-bottomed flask was charged with 240.4 mg (0.58 mmol, 1.0 eq.) of the silyloxy ester 8, dissolved in 4.0 mL of anhydrous toluene, and cooled to −78° C. under argon. To this 1.3 mL (1.2 mmol, 2.2 eq.) of diisobutylaluminum hydride DIBAL-H (1.0M in hexane) was added and stirred at −78° C. for 30 minutes and then at 25° C. for 90 minutes. This was quenched with 5 drops of 2N sodium potassium tartrate, 1.5 mL of water, and diluted with methylene chloride. This was separated, the organic portion dried over anhydrous magnesium sulfate. Purification by silica gel column chromatography (10 to 25% ethyl acetate/hexane) gave 194.2 mg (0.050 mmol, 87%) of the allylic alcohol 9 as a colorless oil (Rf=0.5, 25% ethyl acetate/hexane) which was immediately used in the preparation of E-10 and Z-10. A 25 mL hydrolysis tube was charged with 184.7 mg (0.48 mmol, 1.0 eq.) of the allylic alcohol 6, a total of 427 mg (1.5 mmol, 3.1 eq.) of 1-phenylsulfinyl-2,2,2-triethoxyethane, 3 mg of 2,4,6-trimethylbenzoic acid, and 9 mL of anhydrous methylene chloride. This was sealed under nitrogen and warmed to 135°–145° C. for a total of 12.5 hours. After cooling the reaction mixture, the solvent was evaporated and purification by PTLC (3×1000μ, 3% ethyl acetate/hexane) gave 141.6 mg (0.31 mmol, 65%) of E-10 and 19.9 mg (0.04 mmol, 9%) of Z-10 as oils. Shorter reaction times lead to increased Z/E ratios.

E-10: $^1$H NMR (CDCl$_3$) δ 5.84 (t, J=1.4 Hz, 1H), 5.11 (s, 1H), 4.81 (t, J=1.4 Hz, 1H); $^{13}$C NMR (CDCl$_3$) δ 1.664, 158.0, 149.6, 115.4, 111.4, 66.7, 65.2, 59.6, 42.2, 38.4, 36.5, 25.8 (3C), 25.7 (3C), 18.1, 18.0, 14.3, −4.89, −4.94, −5.48, −5.53; FT-IR (thin film) 1716 cm$^{-1}$; HRMS, m/z (M+-t-Bu) calcd for C$_{24}$H$_{46}$O$_4$Si$_2$ 397.2230, found 397.2235.

Z-10: $^1$H NMR (CDCl$_3$) δ 5.58 (t, 1 Hz, 1H), 4.96–4.93 (m, 2H), 4.15–4.04 (m, 3H), 3.71 (dd, J=10, 5.0 (Hz, 1H), 3.52 (t, 10 Hz, 1H), 2.75–2.68 (m, 1H), 2.44 (ddt, 12.4, 4.0, 1 Hz, 1H), 2.26 (dddd, 12.4, 8.0, 1.6 Hz, 1H), 2.03 (dddd, J=13, 5.6, 4.0, 1.6 Hz, 1H), 1.7 (ddd, 13, 4, 1 Hz, 1H), 1.23 (t, 7.2 Hz, 3H), 0.089 (s, 9H), 0.087 (s, 9H), 0.06 (s, 6H), 0.043 (s, 3H), 0.040 (s, 3H); $^{13}$C NMR (CDCl$_3$) δ 166.3, 154.2, 145.6, 116.4, 112.3, 67.5, 64.2, 60.0, 47.2, 44.0, 36.9, 25.84 (3C), 25.75 (3C), 18.2, 18.0, 14.0, −4.73, −4.80, −5.42, −5.50; FT-IR (CDCl$_3$) 1718 cm$^{-1}$; HRMS, m/z (M+-t-Bu) calcd for C$_{24}$H$_{46}$O$_4$Si$_2$ 397.2230, found 397.2231.

(−) -E-10 from (+)-8: $[α]_D^{23°}$ $^C$ −38.0° (c=0.094, CHCl$_3$, d.e. 98.5%)

(+) -E-10 from (−)-8: $[α]_D^{23°}$ $^C$ −37.2° (c=0.051, CHCl$_3$, d.e. 96.5%)

EXAMPLE 7

Photoisomerization to dienoate Z-10

A borosilicate test tube was charged with 141.1 mg (0.31 mmol) of dienoate E-10, 9.3 mg of 9-fluorenone, and 9.0 mL of tert-butyl methyl ether. The tube was sealed with a rubber septum, placed in a solution of 2M sodium orthovanadate and irradiated with a medium pressure mercury arc lamp for 16 hours. This was purified by PTLC (1×1000μ, 1×1500μ, 3% ethyl acetate/hexane) to give 132.3 mg of an inseparable mixture of Z-10 and 9-fluorenone [therefore, the yield of Z-10 would be 123.0 mg (0.27 mmol, 87%); that is, 132.3 mg of starting material minus 9.3 mg of fluorenone].

EXAMPLE 8

Phosphine oxide 11

A flame-dried round-bottomed flask was charged with 123.0 mg (0.27 mmol, 1.0 eq. containing 9.3 mg of 9-fluorenone) of Z-10 and 1.5 mL of anhydrous toluene under argon and then cooled to 0° C. To this 0.60 mL (0.60 mmol, 2.2 eq.) of diisobutylaluminum hydride DIBAL-H (1M in hexane) was added and stirred at 0° C. for 35 minutes and then warmed to 25° C. An additional 0.06 ml (0.06 mmol, 0.2 eq.) of DIBAL-H was added and stirred for 2 hours. The reaction mixture was quenched with 0.5 mL of 2N sodium potassium tartrate, diluted with methylene chloride, separated, and the organic portion dried over anhydrous magnesium sulfate. Purification by PTLC (2×1000μ), (2 elutions) 10% ethyl acetate/hexane and then 15% ethyl acetate/- hexane gave 56.8 mg (0.14 mmol, 51%) of the allylic alcohol as an oil. A flame-dried 25 mL round-bottomed flask was charged with 90 mg (0.67 mmol, 4.8 eq.) of N-chlorosuccinimide and dissolved in 1.5 mL of anhydrous methylene chloride and then cooled to 0° C. under argon. To this 0.052 mL (0.71 mmol, 5.1 eq.) of dimethyl sulfide was added. The white precipitate that immediately formed was stirred at 0° C. for 10 minutes and then at −20° C. (dry ice/ethylene glycol) for 10 minutes. To this a solution of the freshly prepared allylic alcohol in 1.5 mL of anhydrous methylene chloride was added via cannula (the flask containing the alcohol solution was rinsed with 0.5 mL of anhydrous methylene chloride and this also transferred to the reaction mixture via cannula). This was stirred at −20° C. for 15 minutes and then at 25° C. for 50 minutes. The reaction mixture was quenched with water, diluted with methylene chloride, separated, the organic portion dried over anhydrous magnesium sulfate, filtered, and the solvent evaporated. This was passed through a column of florisil with 10% ethyl acetate/hexane to give 46.7 mg (0.11 mmol, 79%) of the allylic chloride. This was then dissolved in 2.0 mL of anhydrous tetrahydrofuran in a flame-dried 50 mL round-bottomed flask under argon and to this a freshly prepared tetrahydrofuran solution of lithium diphenylphosphide ($Ph_2PLi$, this deep orange reactant was prepared by the quimolar addition of n-butyllithium to diphenylphosphine) was added slowly until a yellow color persisted. This was then quenched with 0.5 mL of water, the tetrahydrofuran evaporated, diluted with 10 mL of methylene chloride, 6 drops of 30% hydrogen peroxide were added, and then rapidly stirred for 10 minutes. This was diluted with methylene chloride, dried over anhydrous magnesium sulfate, filtered, and the solvent evaporated. Purification by silica gel column chromatography (5 to 50% ethyl acetate/hexane) afforded 29.3 mg (0.049 mmol, 45%)(18% from Z-10) of the phosphine oxide 11 as a white solid after removal from benzene, (Rf=0.3, 50% ethyl acetate/hexane), mp 118°-122° C. $^1H$ NMR ($C_6D_6$) δ 7.83-7.78 (m, 4H), 7.05-7.03 (m, 6H), 5.46 (ddt, J=14.0, 7.6, 1.2 Hz, 1H), 5.42 (d, J=2 Hz 1H), 4.99 (dd, J=2, 1.2 Hz, 1H), 3.95-3.90 (m, 1H), 3.69 (dd, J=10.0, 6.4 Hz, 1H), 3.55 (dd, J=10.0, 8.8 Hz, 1H), 3.32-3.12 (m, 2H), 2.70-2.63 (m, 1H), 2.40-2.33 (m, 1H), 2.26-2.19 (m, 1H), 1.94-1.87 (m, 1H), 1.83 (ddd, J=13, 7.6, 4.8 Hz, 1H), 0.98 (s, 9H), 0.95 (s, 9H), 0.071 (s, 3H), 0.065 (s, 3H), 0.049 (s, 3H), 0.014 (s, 3H); $^{13}C$ NMR ($C_6D_6$) δ 145.4 (d, J=2.5 Hz), 142.0 (d, J=12.2 Hz), 132.8 (d, J=98.0 Hz) 132.7 (d, J=98.2 Hz), 131.62 (d, J=2.5 Hz), 131.58 (d, J=2.6), 130.93 (d, J=9.2 Hz), 130.88 (d, J=9.2 Hz), 128.42 (d, J=11.7 Hz), 128.40 (d, J=11.6), 114.0 (d, J=7.8 Hz), 112.6, 67.32, 67.30, 64.1, 46.7, 44.1, 37.4, 31.2 (d, J=70.9 Hz), 25.8 (3C) 25.7 (3C), 18.0 (2C), −4.8, −4.9, −5.4 (2C); IR ($CHCl_3$) 3020, 2956, 2930, 2857, 1680, 1472, 1463, 1438, 1255, 1100 $cm^{-1}$; MS, m/z (EI) 596 ($M^+$, 3), 540 (43), 539 (100), 407 (58), 332 (22), 202 (27), 201 (25), 75 (30), 73 (86); HRMS, m/z ($M^+$) calcd for $C_{34}H_{53}O_3SiP$ 596.3271, found 596.3277.

(−) -11a from (−)-Z-10: $[\alpha]_D^{23.5°}$ C.−54.0° (c=0.061, $CH_2Cl_2$, d.e. 98.5%)

(+) -11a from (+)-z10: $[\alpha]_D^{23.5°}$ C.−54.4° (c=0.096, $CH_2Cl_2$, d.e. 96.5%)

EXAMPLE 9

1α-hydromethyl-25-hydroxyvitamin $D_3$ [(−)-2]

A flame-dried 10 mL round-bottomed flask was charged with 79.7 mg (0.13 mmol, 1.9 eq.) of the phosphine oxide (−)-11a and dissolved in 1.0 mL of freshly distilled anhydrous tetrahydrofuran and cooled to −78° C. under argon. Phosphine oxide (−)-11a was azeotropically dried with benzene and held under high vacuum for 24 hours immediately prior to use. To this 0.091 mL (0.138 mmol, 2.0 eq.) of PhLi (1.52M in diethyl ether) was added dropwise over a 5 minute period. A deep orange-red color persisted after the second drop of the PhLi solution was added. This was allowed to stir an additional 8 minutes at −78° C. at which time a precooled (−78° C.) solution consisting of 24.3 mg (0.069 mmol, 1.0 eq.) of the CD ring ketone in 0.5 mL of freshly distilled anhydrous tetrahydrofuran was added dropwise via cannula. The C,D ring ketone 12 was also azeotropically dried with benzene and held under high vacuum immediately prior to use. The flask containing the C,D ring ketone 12 was rinsed with 0.4 mL of tetrahydrofuran and this was also slowly added to the reaction mixture via cannula. This deep orange-red solution was stirred in the dark at −78° C. for 2.5 hours and then warmed to −65° C. over 30 minutes. At this temperature, the reaction mixture turned to a light yellow. This was immediately quenched with 0.3 mL of 2N sodium potassium tartrate followed by the addition of dilute aqueous potassium carbonate. After warming to room temperature, the reaction was diluted with methylene chloride, separated, the organic portion dried over anhydrous magnesium sulfate, and filtered. Purification by silica gel column chromatography (5% to 10% ethyl acetate/hexane) afforded 37.9 mg (0.049 mmol, 69%) of the crude coupled product. This was immediately placed in a flame-dried 10 mL round-bottomed flask and dissolved in 3.0 mL of freshly distilled anhydrous tetrahydrofuran under argon. To this 0.17 mL (0.17 mmol, 3.5 eq.) of tetrabutylammonium fluoride (1M in tetrahydrofuran) was added and stirred at 25° C. in the dark for 14 hours. The solvent was evaporated and the crude product passed through a column of silica gel with 5% to 10% methanol/diethyl ether and then purified by PTLC (3×1000μ, 8% methanol/diethyl ether) to afford 17.2 mg (0.039 mmol, 83%) [58% from (−)-11a] of 1α-hydroxymethyl-25-hydroxyvitamin $D_3$ [(−)-2]. This compound was only sparingly soluble in organic solvents (e.g. MeOH, $CHCl_3$, $CH_2Cl_2$). $^1H$ NMR ($CDCl_3$) δ 6.32 (d, J=11.2 Hz, 1H), 5.95 (d, J=11.2 Hz, 1H), 5.18 (d, J=2 Hz, 1H), 5.02 (d, J=2 Hz, 1H), 0.93 (d, J=6.4 Hz, 3H), 0.54 (s, 3H). $^{13}C$ NMR ($CD_3OD$) δ 147.7, 142.6, 136.7, 124.0 119.0, 114.1, 71.5, 67.4, 64.7, 58.0, 57.6, 47.4, 47.0, 46.5, 45.3, 41.9, 37.8, 37.6, 37.5, 30.0, 29.3, 29.1, 28.7, 24.7, 23.3, 22.0, 19.4, 12.3; UV (EtOH) λmax 264 nm; mp 181°-184° C.

EXAMPLE 10

1β-hydroxymethyl-3β-norhydroxy-3α,25 dihydroxyvitamin $D_3$ [(+)-3]

This procedure was similar to the one used for the preparation of vitamin 2. The amounts of reagents utilized were as follows:

phosphine oxide (+)-11b: 101.3 mg(0.17 mmol, 2.7 eq.), PhLi (1.52M in $Et_2O$): 0.135 mL (0.21 mmol, 3.3 eq.), C,D ring 12: 22.3 mg (0.063 mmol, 1.0 eq.)

This afforded 21.1 mg (0.049 mmol, 76%) of the vitamin (+)-3 as an off white solid. $^1$H NMR (CDCl$_3$) δ 6.31 (d, J=11.3 Hz, 1H), 5.94 (d, J=11.3 Hz, 1H), 5.15 (dd, J=2.1, 1.0 Hz, 1H), 4.99 (d, J=2 Hz, 1H), 4.03-3.97 (m, 1H), 3.63-3.55 (m, 2H), 2.83-2.78 (m, 1H), 2.65-2.57 (m, 1H), 2.30-2.24 (m, 1H), 0.93 (d, J=9.8 Hz, 3H), 0.5 (s, 3H); $^{13}$C NMR (CDCl$_3$) δ 145.4, 143.3, 134.1, 123.7 117.0, 113.9, 71.1, 67.2, 64.4, 56.5, 56.3, 46.3 45.9, 44.5, 40.5, 37.5, 36.4, 36.1, 29.4, 29.2, 29.1, 27.7, 23.6, 22.3, 20.8. 18.8, 11.9; UV (EtOH) λmax 264 nm; mp 118°-123° C.

The 1-hydroxymethyl derivatives of the invention have been compared with calcitriol for biological activity. The compounds were tested for growth inhibition of murine keratinocyte cells (cell line PE) and for the inhibition of TPA-induced ornithine decarboxylase (ODC) activity.

The cell line PE was derived from a papilloma induced in female SENCAR mice by a standard skin initiation/promotion protocol (*Carcinogenesis*, 7:949-958 (1986)) and was chosen for its particular sensitivity to the induction of ornithine decarboxylase (ODC) activity by the extensively characterized tumor promoter TPA. The PE cell line culture medium used in the tests consisted of Eagle's minimal essential medium without calcium chloride supplemented with 8% chelexed fetal calf serum and 1% antibiotic-antimycotic and the addition of CaCl$_2$ to 0.05 mM Ca$^{++}$.

Growth Inhibition Test

The growth inhibition test was carried out as follows:

Growth curves for PE cells treated with calcitriol and its 1-hydroxymethyl homologs were generated by assay for the reduction of 3-(4,5-dimethylthiazol-2-yl)-2,5-diphenyltetrazolium bromide (MTT) according to the method described by Carmichael et al, *Cancer Res.*, 47:936-942 (1987). A mitochondrial dehydrogenase reduces MTT to a blue formazan product with an absorbance maximum of 505 nm in DMSO; the number of viable cells can thus be determined spectrophotometrically.

PE cells were seeded at a density of 5,000 cells/well in 50 µl medium into 96-well microtiter plates. Twelve hours later, the medium was removed, and cells were treated with 100 µl fresh medium into which the appropriate amount of vitamin D$_3$ or derivative dissolved in dimethyl sulfoxide (DMSO) had been added, with the concentration of DMSO held constant at 0.1%. The plates were fed once at 48 hours, with the readdition of the vitamin D$_3$ analogues at this time. At 24 hour intervals following the initial treatment of the cells with compounds, 0.1 mg (50 µg of a 2 mg/ml solution) of MTT was added to the plates. After 4 hours, the MTT was removed and DMSo added to dissolve the blue formazan dye. Using a microtiter plate reader, the A$_{505}$ was then determined and cell number calculated from blank-subtracted absorbance values. Results from the MTT assay for the inhibition of cell growth were independently confirmed by treating 100 cm$^2$ dishes of cells in an analogous manner for 96 hours, whereupon the cells were harvested by trypsinization and counted. Further, the viability of the cells treated with vitamin D$_3$ or derivatives was determined to be identical to control cells at 96 hours by trypan blue exclusion.

Inhibition of TPA-induced ODC Activity 100 cm$^2$ dishes of PE cells were treated with vitamin D$_3$ or analogues dissolved in DMSO by direct addition into the culture medium. Fifteen minutes later, the plates were treated with 100 ng/ml TPA dissolved in ethanol. For both additions, the solvent concentration was held constant at 0.1%, and control values represent the results from plates treated with these solvents. Three plates were used for each experimental group. Following incubation for 4 hours after addition of TPA, the medium was removed and the dishes washed with ice cold phosphate-buffered saline (PBS). The excess PBS was then removed and the dishes rinsed with an ice cold solution of pyridoxal phosphate in PBS (50 µg/ml). The excess liquid was removed, and the dishes were frozen at −80° C. The dishes were scraped into Eppendorf tubes while still partially frozen, and the cells further lysed by freeze-thawing for generation of the 12,000×g cytosol. Cytosolic ODC activity was determined in triplicate by measuring the release of $^{14}$CO$_2$ from L-[$^{14}$C]ornithine using an Eppendorf microvessel assay as previously described (*Cancer Res.*, 43:2555-2559 (1983)).

Results

Results of the foregoing tests are illustrated by the accompanying drawings wherein:

FIG. I graphically shows the growth inhibition of keratinocyte cell line PE by vitamin D$_3$ and 1-hydroxymethyl homologs at 3 µM. The values shown represent the mean from 12 wells±S.D. Arrows indicate administration of fresh medium into which the compounds dissolved in DMSO had been added. Control cells were treated with DMSO alone (0.1% in culture medium). The treated values are significantly different from the solvent control at 72 and 96 hours (p 0.001, Student's t-test).

FIG. II illustrates the inhibition of TPA-induced ornithine decarboxylase activity by pretreatment with vitamin D$_3$ and 1-hydroxymethyl homologs. FIG. II A shows inhibition of TPA-stimulated response by pretreatment of cells for 15 minutes with 1 µM of the compounds. Values represent the mean ±S.D. for 3 measurements. Pretreatment with calcitriol or its synthetic derivatives resulted in a statistically significant reduction in TPA-induced ODC activity (p<0.001, Student's t-test). FIG. II B shows a dose-response curve for the inhibition of TPA-induced ODC activity with the 1-hydroxymethyl vitamin D$_3$ diastereomers (−) -2 and (+)-3.

As shown, calcitriol and its 1-hydroxymethyl derivatives were equipotent at inhibiting growth of PE cells. The antiproliferative effects of the three compounds as demonstrated by reduction in cell number over time as compared to control plates is shown in FIG. I. While the control cells continued in the exponential phase of cell growth from 24 hours onward, this rapid rate of cell proliferation was significantly blunted by treatment with calcitriol or its 1-hydroxymethyl derivatives. Further, the treated cell populations had reached a plateau by 72 hours, days before the control cells would become confluent and senescent. Thus all three vitamin D$_3$ compounds were active in inhibiting cell growth and division. The activity of these compounds was due to cytostatic rather than cytotoxic effects, as cell viability was unchanged in the treatment groups as determined by dye exclusion assay.

Calcitriol and the 1-hydroxymethyl diastereomers also significantly inhibited the effects of TPA (12-O-tetradecanoylphorbol-13-acetate) on the activity of ornithine decarboxylase (ODC). ODC catalyzes the initial and rate-limiting step in the polyamine biosynthetic pathway; while the function of polyamines is not fully understood, they are essential for growth, differentiation and replication. This enzyme can be induced rapidly and dramatically by many growth stimuli, including the tumor promoter TPA (*Annu. Rev. Biochem.,* 53:749–790 (1984)). The ability of TPA to induce ODC is associated with its proliferative and tumor-promoting properties (*Cancer Res.,* 35:2426–2433 (1975); *Biochem. Biophys. Res. Commun.,* 105:969–976 (1982) and *Proc. Natl. Acad. Sci. USA,* 70:6028–6032 (1982)). A variety of agents have been shown to inhibit TPA effects on ODC induction as well as TPA-stimulated tumor promotion, including calcitriol (*Cancer Res.,* 45:5426–5430 (1985); *Biochem. Biophys. Res. Commun.,* 116:605–611 (1983)) anti-inflammatory steroids and vitamin A analogues (*Biochem. Biophys. Res. Commun.,* 91:1488–1496 (1979)), as well as free radical scavenging compounds (*Adv. Free Radical Biol. and Med.,* 2:347–387 (1986)). Similarly, FIG. II shows the effects of vitamin $D_3$ and its 1-hydroxymethyl derivatives on the TPA-stimulated ODC activity in vitro. The potency of the three compounds as inhibitors of the effects of TPA on this enzyme were not significantly different from each other. FIG. II B of FIG. II illustrates the similar dose-response characteristics of the 1-hydroxymethyl vitamin $D_3$ diastereomers.

Taken together, these results indicate that replacing the 1α-hydroxyl group in calcitriol does not diminish biological activities characteristic of vitamin $D_3$. Further, the results demonstrate that changing the stereochemistry of a 1-substituent (i.e., 1α->1β2->3) does not necessarily change antiproliferative activity.

The foregoing shows unexpectedly high antiproliferative and cell growth inhibitory activities for the 1-hydroxyalkyl analogues of the invention, the expectation from the prior art being that replacement of the 1α-hydroxyl group of calcitriol would be damaging to such activities. It is also surprising that changing the stereochemistry of the 1-hydroxyalkyl (1α to 1β, compound 2 to compound 3) did not change the antiproliferative or cell growth inhibitory activity. Both (−)-2 and (+)-3 showed less than, or equal to, 2% of calcitriol's binding to the 1,25(OH)$_2$-vitamin $D_3$ receptor.

It will be appreciated that various modifications may be made in the foregoing without departing from the spirit and scope of the invention as defined in the following claims wherein:

What is claimed is:

1. A vitamin $D_3$ analogue of the formula:

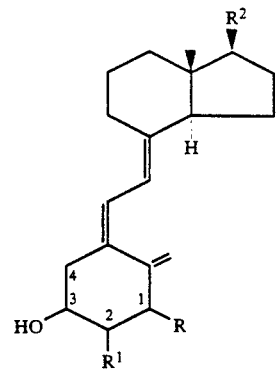

and stereoisomers thereof, wherein R is —$R^3$OH where $R^3$ is straight or branched alkyl of 1 to 6 carbons, $R^1$ is hydrogen and $R^2$ represents a 25-hydroxy $D_3$ side chain.

2. An analogue according to claim 1 which is 1-hydroxymethyl-25-hydroxyvitamin $D_3$ of the formula:

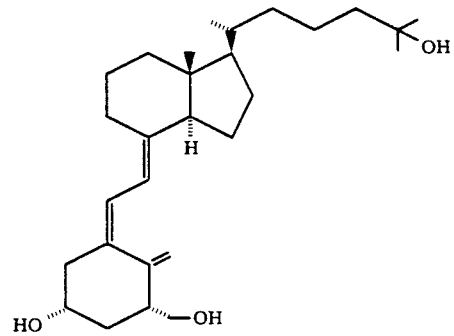

or the formula:

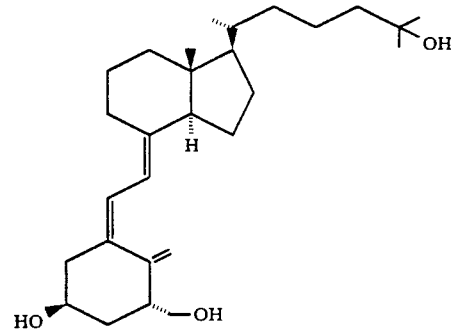

* * * * *